(12) United States Patent
Miller et al.

(10) Patent No.: US 10,830,401 B2
(45) Date of Patent: Nov. 10, 2020

(54) MEDICAL EXAMINATION LIGHT FIXTURE

(71) Applicant: Hubbell Incorporated, Shelton, CT (US)

(72) Inventors: Eric Miller, Simpsonville, SC (US); David Rector, Mauldin, SC (US); Chris Bailey, Greenville, SC (US); John Hollander, Greenville, SC (US); Raymond Brown, Greer, SC (US)

(73) Assignee: Hubbell Incorporated, Shelton, CT (US)

( * ) Notice: Subject to any disclaimer, the term of this patent is extended or adjusted under 35 U.S.C. 154(b) by 42 days.

(21) Appl. No.: 15/490,254

(22) Filed: Apr. 18, 2017

(65) Prior Publication Data
US 2017/0303357 A1 Oct. 19, 2017

Related U.S. Application Data

(60) Provisional application No. 62/324,066, filed on Apr. 18, 2016.

(51) Int. Cl.
| | |
|---|---|
| *F21S 8/02* | (2006.01) |
| *A61B 90/35* | (2016.01) |
| *F21V 7/00* | (2006.01) |
| *H05B 45/10* | (2020.01) |
| *H05B 45/00* | (2020.01) |
| *F21W 131/208* | (2006.01) |
| *F21Y 115/10* | (2016.01) |

(Continued)

(52) U.S. Cl.
CPC .............. *F21S 8/026* (2013.01); *A61B 90/35* (2016.02); *F21V 7/0016* (2013.01); *H05B 45/00* (2020.01); *H05B 45/10* (2020.01); *F21V 7/005* (2013.01); *F21W 2131/208* (2013.01); *F21Y 2103/10* (2016.08); *F21Y 2113/00* (2013.01); *F21Y 2115/10* (2016.08)

(58) Field of Classification Search
CPC .................................. F21S 8/026; F21V 5/04
See application file for complete search history.

(56) References Cited

U.S. PATENT DOCUMENTS

| | | |
|---|---|---|
| 4,933,820 A | 6/1990 | Engel |
| 5,038,254 A | 8/1991 | Fabbri et al. |
| 7,594,736 B1 | 9/2009 | Kassay et al. |

(Continued)

OTHER PUBLICATIONS

PCT/US2017/028085 International Search Report and Written Opinion dated Jul. 26, 2017 (13 pages).

*Primary Examiner* — Evan P Dzierzynski
(74) *Attorney, Agent, or Firm* — Michael Best & Friedrich, LLP

(57) ABSTRACT

A ceiling mounted light fixture includes a lens assembly including a central lens and a pair of side lenses. The central lens extends along a longitudinal axis, and each side lens extends parallel to the central lens and is positioned on a lateral side of the central lens. The fixture further includes at least one central light emitter for emitting light directly through the central lens and a pair of side light emitters. At least one control component operatively connected to the central light emitter and the side light emitters is configured to operate in a first mode in which the central light emitter is deactivated and the side light emitters are activated, and a second mode in which the central light emitter and the side light emitters are activated.

20 Claims, 15 Drawing Sheets

(51) Int. Cl.
*F21Y 103/10* (2016.01)
*F21Y 113/00* (2016.01)

(56) References Cited

U.S. PATENT DOCUMENTS

| | | |
|---|---|---|
| 2010/0277105 A1 | 11/2010 | Oyama |
| 2013/0308308 A1 | 11/2013 | Prltchett |
| 2014/0016340 A1* | 1/2014 | Cho .................... F21S 41/141 362/516 |
| 2015/0377461 A1* | 12/2015 | Hutchins ................ F21V 21/03 362/237 |

* cited by examiner

MEDICAL EXAMINATION LIGHT FIXTURE

CROSS-REFERENCE TO RELATED APPLICATION

This application claims the benefit of, prior-filed U.S. Provisional Application No. 62/324,066, filed Apr. 18, 2016, the entire contents of which are incorporated by reference herein.

BACKGROUND

The application relates to a ceiling-mounted light fixture.

Conventional light fixtures for commercial environments may include a troffer that is mounted into a drop-ceiling or hard ceiling and contains a light source for providing overhead illumination.

SUMMARY

In one aspect, a ceiling mounted light fixture includes a housing having an upper wall and a plurality of side walls at least partially defining an opening, the housing extending along a longitudinal axis; a lens assembly including a central lens and a pair of side lenses, the central lens extending along the longitudinal axis of the housing, each side lens extending parallel to the central lens and positioned on a lateral side of the central lens; at least one central light emitter for emitting light directly through the central lens; a pair of side light emitters, light emitted by each side light emitter passing through an associated one of the side lenses; and at least one control component operatively connected to the at least one central light emitter and the side light emitters. The at least one control component is configured to operate in a first mode in which the at least one central light emitter is deactivated and the side light emitters are activated, and a second mode in which the at least one central light emitter and the side light emitters are activated.

In another aspect, a ceiling mounted light fixture includes a housing having an upper wall and a plurality of side walls at least partially defining an opening, a light emitter assembly positioned in the opening and secured to the housing, and at least one control component operatively connected to the central light emitters, the first side light emitters, and the second side light emitters. The light emitter assembly includes a central portion including a plurality of central light emitters aligned along an axis, a first side portion positioned on one side of the central portion and including a plurality of first side light emitters aligned in a direction parallel to the axis, a second side portion positioned on another side of the central portion and including a plurality of second side light emitters aligned in a direction parallel to the axis, and a lens assembly including a central lens, a first side lens, and a second side lens. The central lens is positioned adjacent the plurality of central light emitters. The first side lens positioned adjacent the plurality of first side light emitters, and the second side lens is positioned adjacent the plurality of second side light emitters. The at least one control component is configured to operate in a first mode in which the first side light emitters and the second side light emitters are activated and is configured to operate in a second mode in which the first side light emitters, the second side light emitters, and the central light emitters are activated.

In yet another aspect, a method for controlling operation of a light fixture includes: determining which mode of a plurality of modes is selected; while a first mode is selected, activating a plurality of first side light emitters, activating a plurality of second side light emitters, and deactivating a plurality of central light emitters positioned between the first side light emitters and the second side light emitters; and while a second mode is selected, activating the plurality of first side light emitters, the plurality of second side light emitters, and the plurality of central light emitters.

The above-described and other features and advantages of various exemplary embodiments of the present disclosure will be appreciated and understood by those skilled in the art from the following detailed description and drawings.

Figure 1:
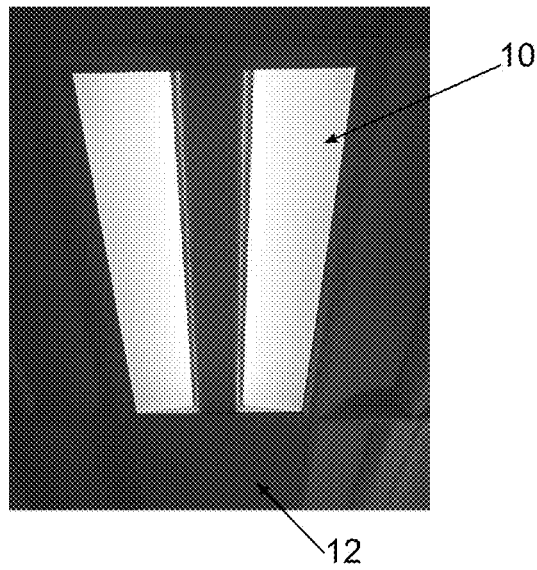
FIG. 1 is a lower perspective view of a light fixture.

Before any embodiments are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. Use of "including" and "comprising" and variations thereof as used herein is meant to encompass the items listed thereafter and equivalents thereof as well as additional items. Use of "consisting of" and variations thereof as used herein is meant to encompass only the items listed thereafter and equivalents thereof. Unless specified or limited otherwise, the terms "mounted," "connected," "supported," and "coupled" and variations thereof are used broadly and encompass both direct and indirect mountings, connections, supports, and couplings.

DETAILED DESCRIPTION

Various embodiments are directed to light fixtures used for patient room and patient examination lighting. For patients and health care professionals, lighting is important for patient experience, observation accuracy, procedure success, patient recovery, patient safety (slips, trips and falls, etc.) and for general patient comfort.

Figure 2:
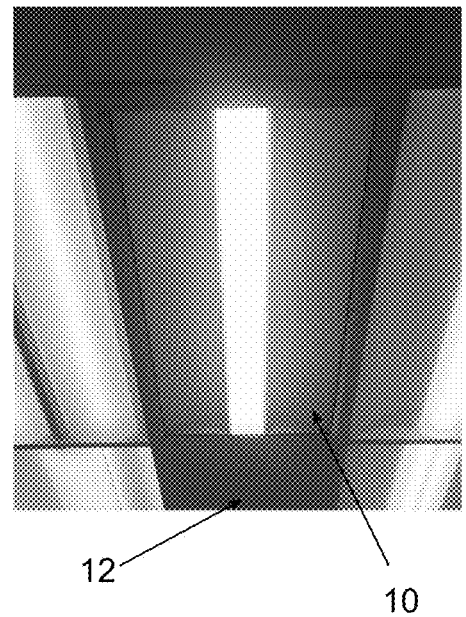
FIG. 2 is a lower perspective view of the light fixture of FIG. 1 in ambient mode.
Figure 3:
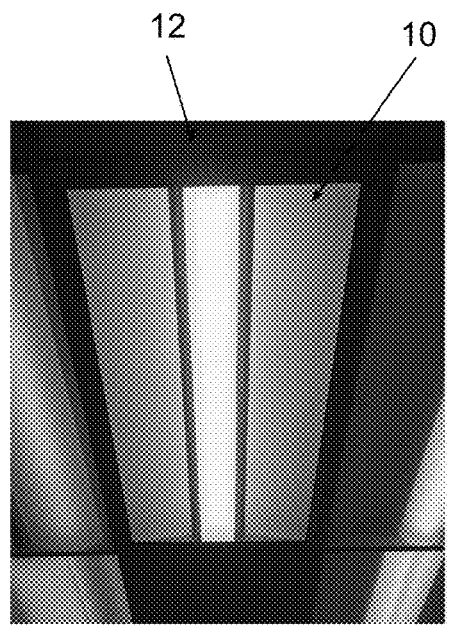
FIG. 3 is a lower perspective view of the light fixture of FIG. 1 in a combination mode.

FIGS. 1-3 depict and exemplary light fixture 10 that is capable of producing more than one output modes. The light fixture 10 is installed in a surface, for example a ceiling or drop ceiling 12. The light fixture 10 may be recessed or surface mounted and is electrically connected to a power source (not shown), such as a mains power supply. FIG. 1 shows the fixture 10 in a first mode or ambient mode of operation that provides soft or diffused light from side portions of the light fixture. FIG. 2 shows the fixture 10 in a second mode or examination mode of operation that provides direct, downward light to a specific area for patient examination. FIG. 3 shows the fixture in a third mode or combination mode of operation that provides both ambient light and examination light. The light fixture 10 may also be capable of operating in a reading mode, which has a light output that is similar to, but brighter than, the ambient mode shown in FIG. 1.

Figure 4:
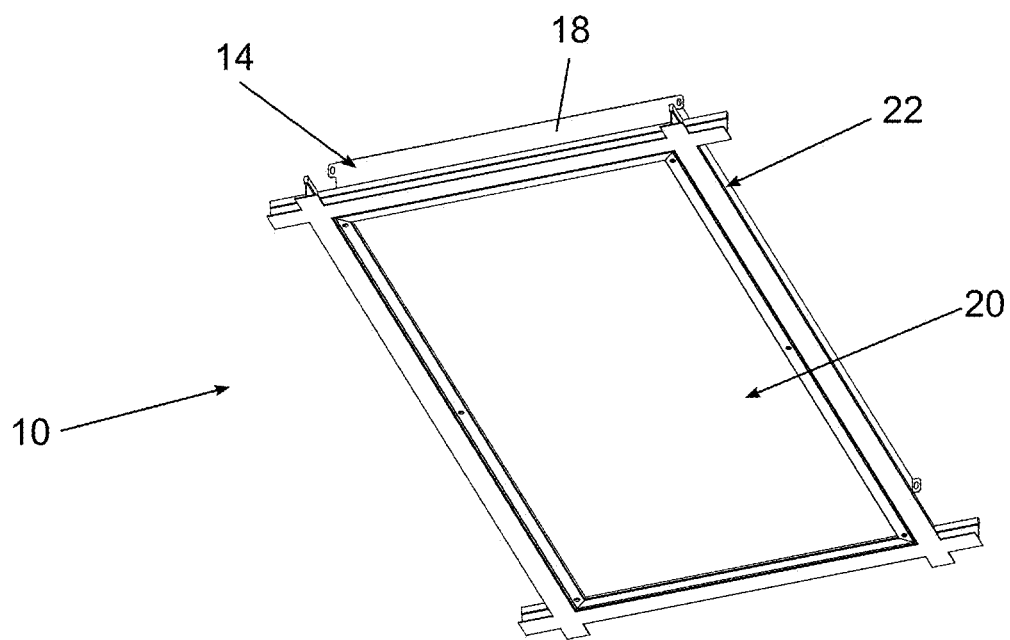
FIG. 4 is a lower perspective view of a light fixture and frame.
Figure 5:
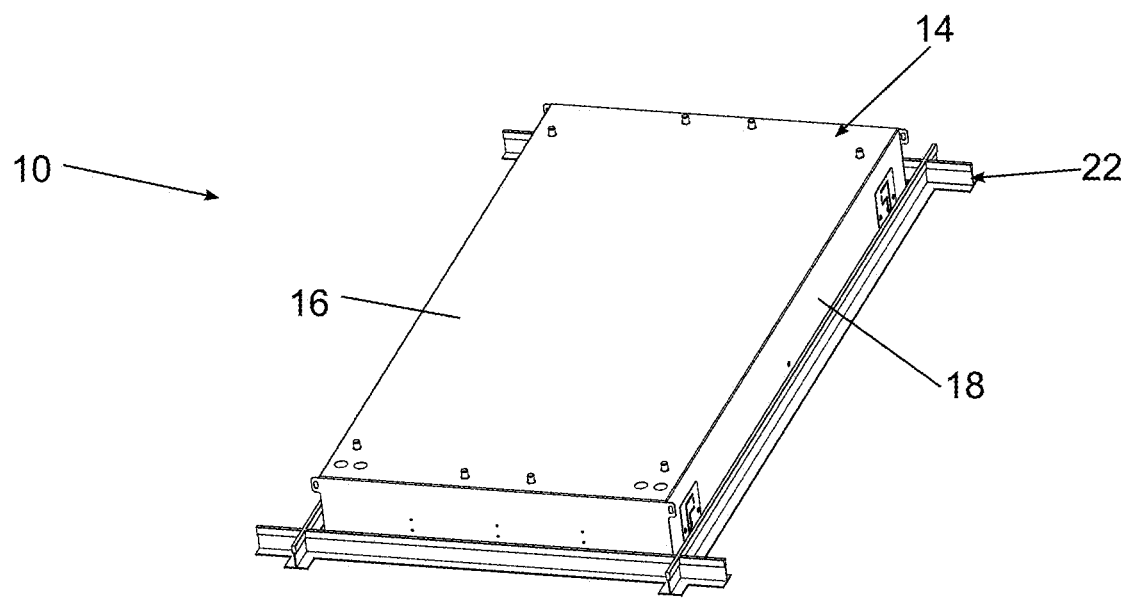
FIG. 5 is an upper perspective view of the light fixture and frame FIG. 4.

FIGS. 4 and 5 show the light fixture 10 removed from the ceiling 12 (FIG. 3). The light fixture 10 includes a housing 14 having one or more top walls 16 and one or more side walls 18 at least partially defining an interior compartment. The top wall 16 and the side walls 18 each have a rectilinear configuration and are oriented at right angles to form a substantially rectangular housing 14. In other embodiments, other rectilinear and curvilinear configurations and orientations can be used. The housing 14 is shown as having a standard 2×4 configuration. Other standard configurations, for example 1×4 and 2×2, and non-standard configurations can also be used.

Figure 5A:
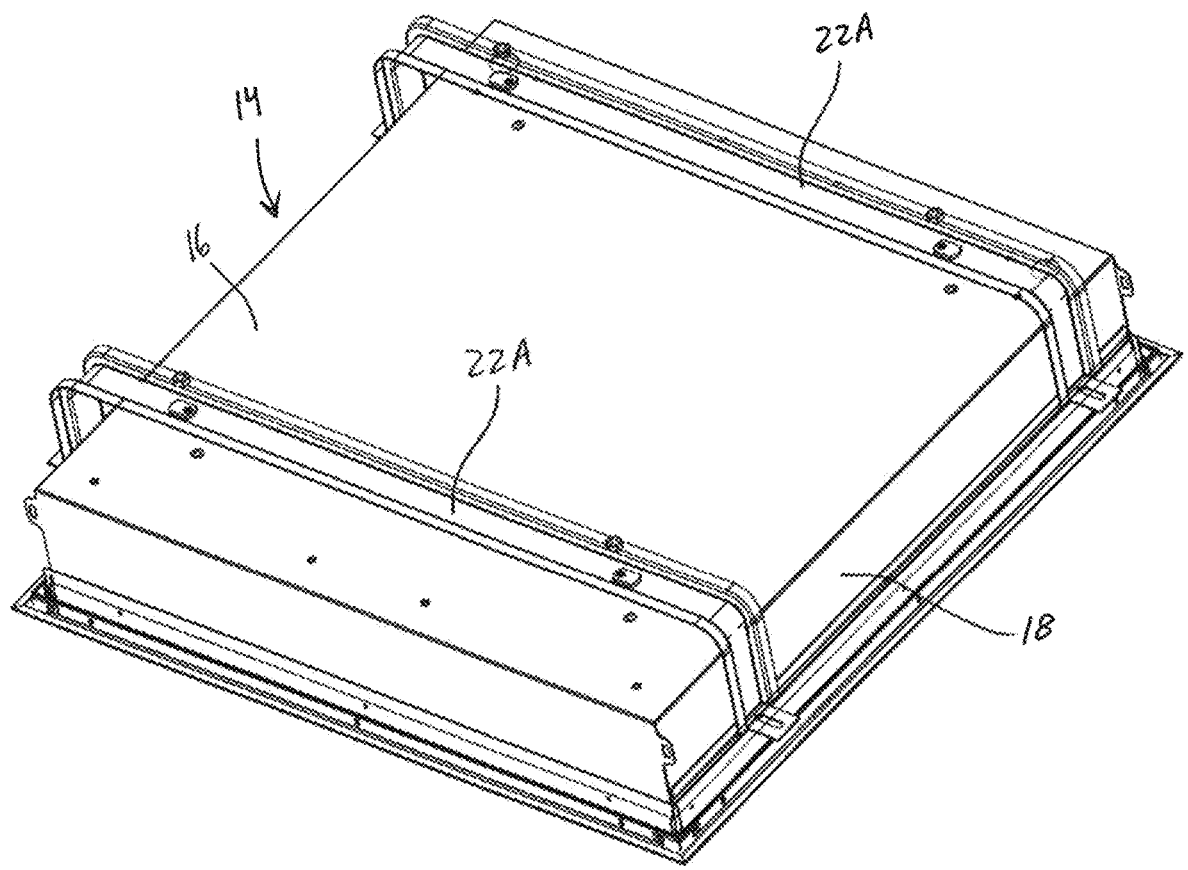
FIG. 5A is an upper perspective view of a light fixture including a support according to another embodiment.

Light emitters and one or more control components are positioned in the interior of the housing 14. The light emitters produce and emit light through an open portion of the housing 14. An outer lens 20 can be positioned over the open portion. The outer lens 20 can be plain and completely transparent, or it can include features that direct, diffuse, color, or otherwise alter the light leaving the housing 14. In the embodiment shown in FIGS. 4 and 5, a grid frame 22 extends along a perimeter of the housing 14 and supports the housing 14 in the ceiling 12; in other embodiments (FIG. 5A), one or more flanges 22A extend along an upper surface of the housing 14 and support the housing 14 relative to a ceiling.

Figure 6:
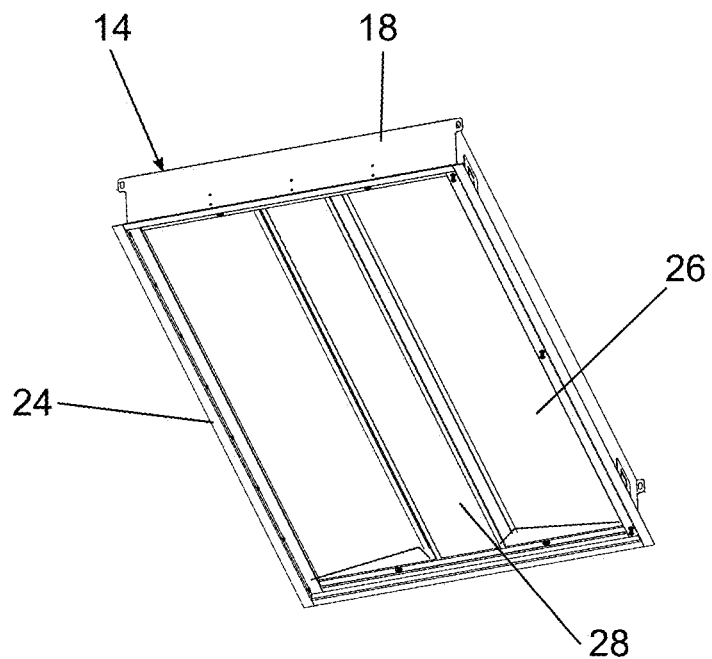
FIG. 6 is a lower perspective view of FIG. 4 with the frame and an outer lens removed.

FIG. 6 shows the housing 14 separated from the frame 22 and with the outer lens 20 removed. One or more flanges 24 extend from the side walls 18 to position and/or support the housing 14 in the frame 22. A single continuous flange 24 can extend around the entire housing or multiple discrete flanges can be used extending from one or more of the side walls 18. The flanges 24 are shown as flush with a lower edge of the housing 14, but may also be offset to accommodate ceiling tiles in a drop ceiling. In alternative embodiments, the flange 24 is removed and the housing 14 is mounted in any other suitable manner.

In an exemplary embodiment, the light fixture 10 can include an internal lens or lens assembly. FIG. 6 shows an internal lens assembly with a pair of side lenses 26 and a central lens 28. The internal lens assembly can be held in place by one or more frame elements. The side lenses 26 and central lens 28 may be plain and completely transparent, or they can include features that direct, diffuse, color, or otherwise alter light passing therethrough. In conjunction with the embodiments shown in FIGS. 1-3, the side lenses 26 can be used to diffuse light for the ambient lighting shown in FIG. 1 and the central lens 28 can be used to direct or focus light for the examination lighting shown in FIG. 2.

Figure 7:
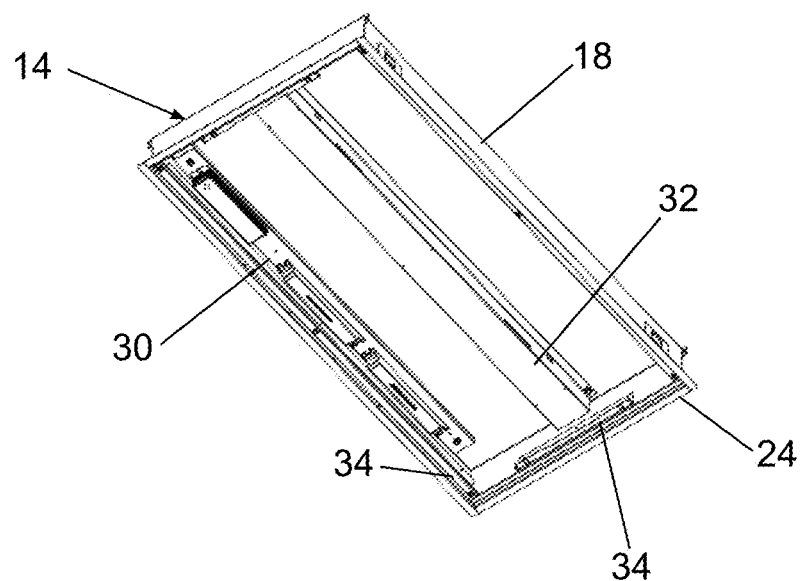
FIG. 7 is a lower perspective view of a housing.

FIG. 7 shows an exemplary embodiment of the housing 14 interior that includes a tray 30. The tray 30 is positioned in the housing 14 to support one or more control components. The tray 30 can be releasably connected to the top wall 16, for example by one or more fasteners. The exemplary embodiment shows three drivers mounted on the tray 30 that are associated with one or more light emitters. For example, one driver can power the light emitters in exam mode, one driver can power the light emitters in ambient mode, and another driver can power the light emitters in reading mode. Other control components can be mounted to the tray 30 or positioned elsewhere in the housing. For example, a low voltage controller can be provided that is operated by a user to switch the light fixture 10 between different modes. Other control components can be used including, drivers, surge protectors, fuses, batteries, photocells, occupancy sensors, wireless communication devices, or any combination thereof. The tray 30 allows for easy changing and maintenance of the control components.

The interior of the housing 14 also includes a central bracket 32 and one or more side brackets 34. The central bracket 32 extends from the top wall toward the opening and runs along the length of the housing 14. A shown in FIGS. 8 and 9, a light emitter assembly 40, or a portion thereof, can be connected to the central bracket 32. The central bracket 32 can also be used to at least partially support a reflector 42. For example, a tab 43 extending from the reflector 42 can be positioned in a slot in the central bracket 32.

Figure 8:
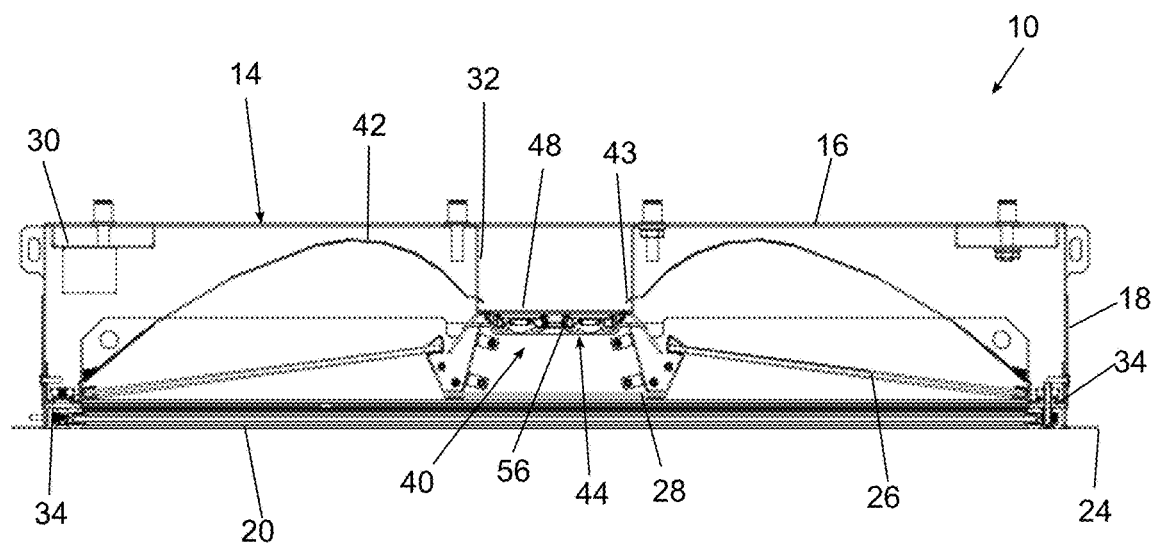
FIG. 8 is a side sectional view of the light fixture of FIG. 4.
Figure 9:
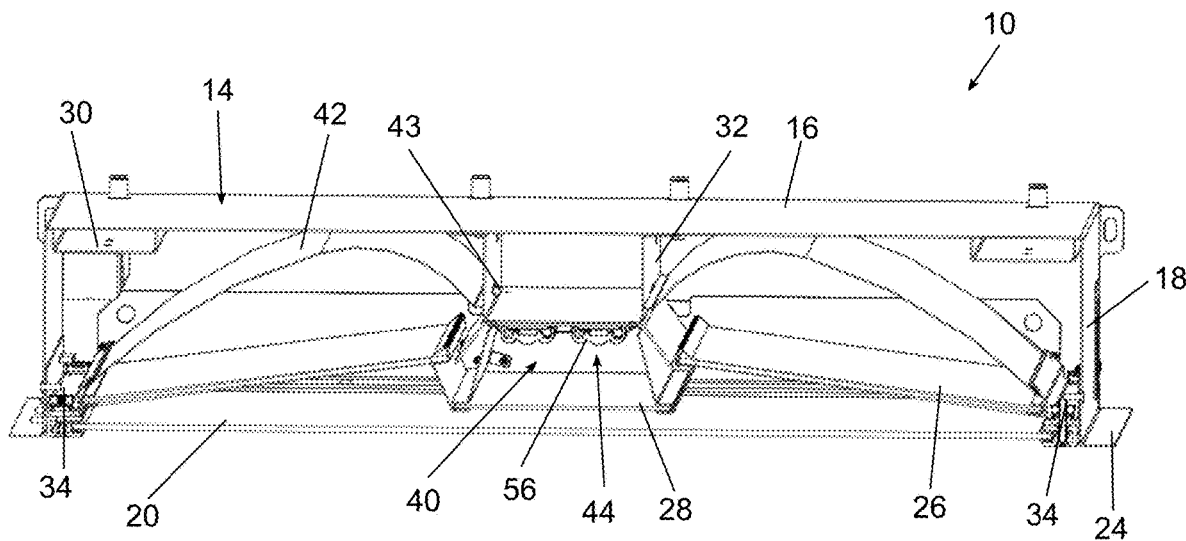
FIG. 9 is a side perspective, sectional view of the light fixture of FIG. 4.
Figure 10:
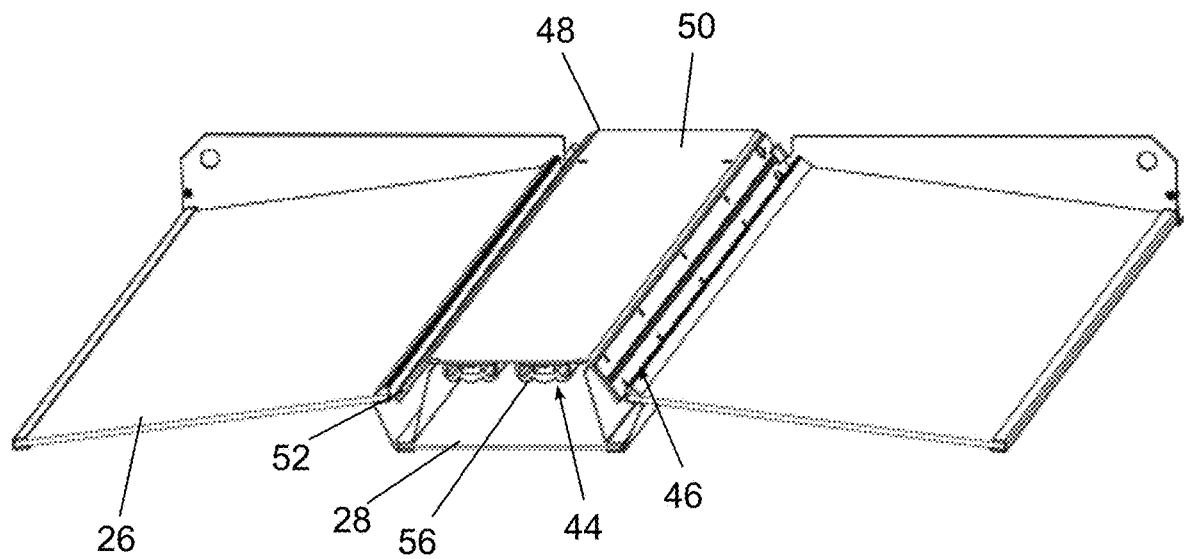
FIG. 10 is an upper perspective view of a light emitter assembly and internal lens assembly.
Figure 11:
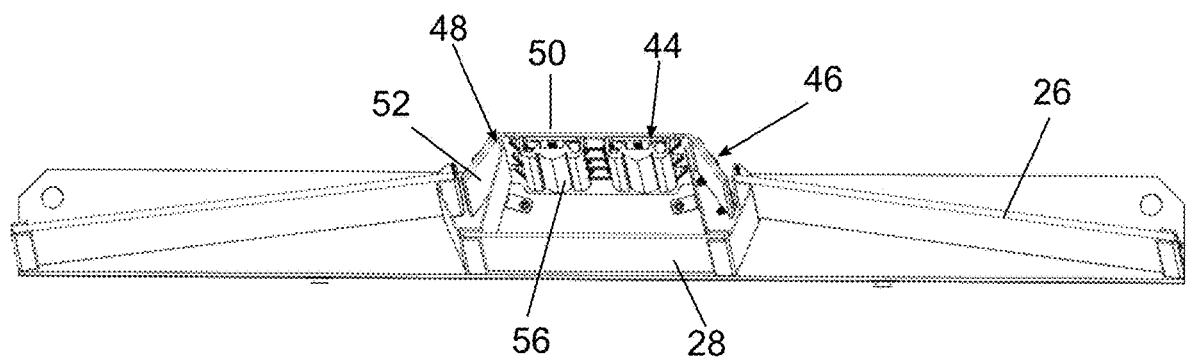
FIG. 11 is a lower perspective view of the light emitter assembly of FIG. 10.
Figure 12:
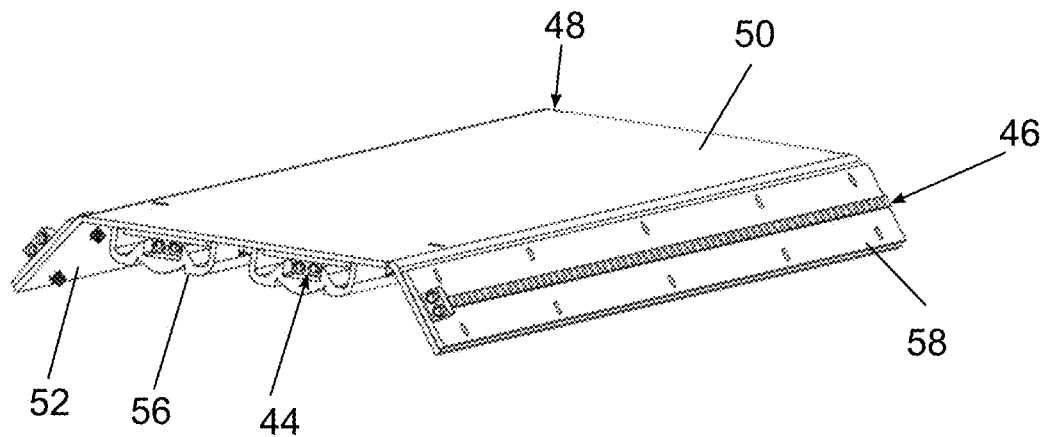
FIG. 12 is an upper perspective view of a light emitter assembly.
Figure 13:
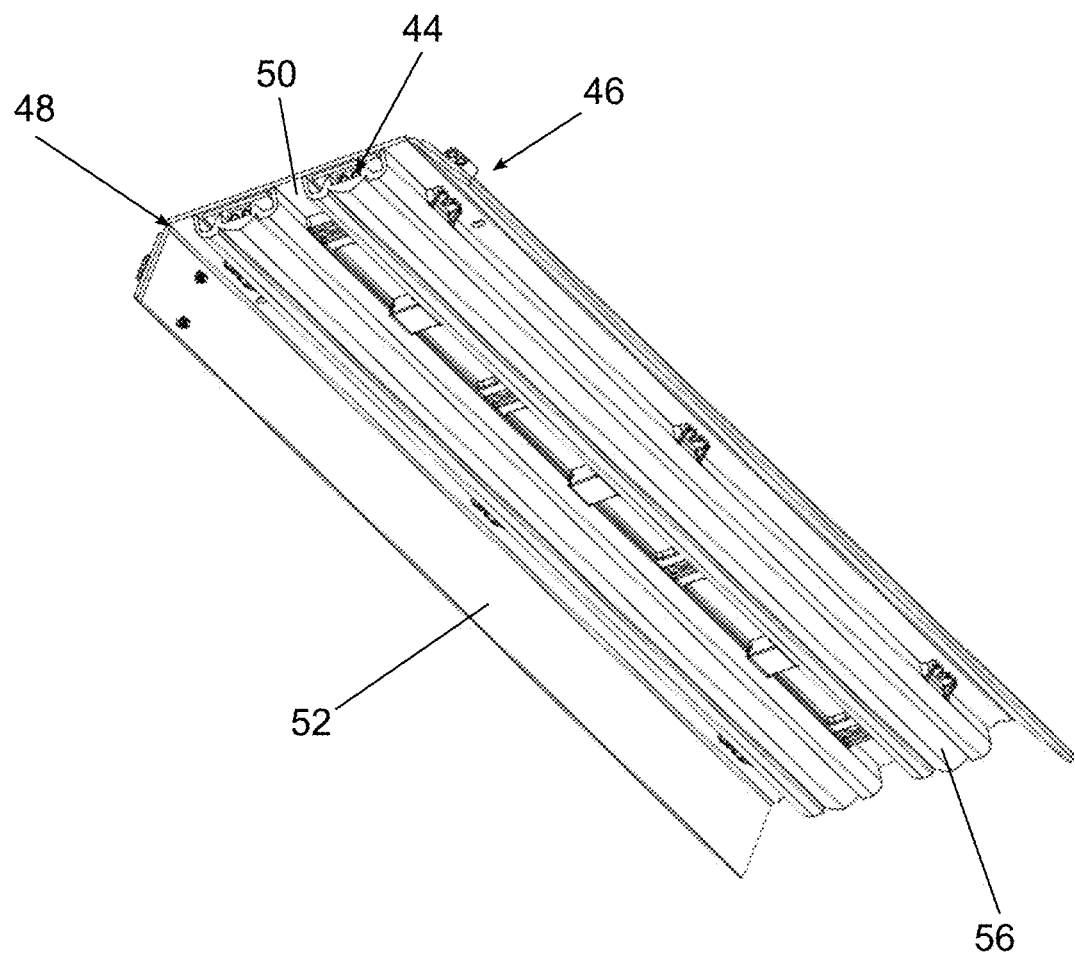
FIG. 13 is a lower perspective view of the light emitter assembly of FIG. 12.

The one or more side brackets 34 extend from one or more of the side walls 18. In the exemplary embodiment, a side bracket 34 extends from each of the four side walls 18. The side brackets 34 are used to connect and support various components, including the outer lens 20, the inner lens assembly, and the reflectors 42 as shown in FIGS. 8 and 9. These components can be directly connected to the side brackets 34 or connected through various mounting components as would be understood by one of ordinary skill in the art.

In an exemplary embodiment, the light emitter assembly 40 includes one or more central light emitters 44 and a pair of side light emitters 46 connected to a support 48. The central light emitters 44 are configured to emit light downward toward the housing opening through the central lens 28. The side light emitters 46 are configured to emit light upward, at an angle, toward the reflectors 42. The light emitted from the side light emitters 46 is reflected off the reflectors and directed downward toward the housing opening through the side lenses 26.

FIGS. 12-15 show the light emitter assembly 40. The support 48 includes a central portion 50 supporting the central light emitters 44 and a pair of sides 52 supporting the side light emitters 46. The sides 52 are oriented at an oblique angle to the central portion 50. The exact angle can be varied depending on the desired light output and of internal layout of the luminaire 10.

Figure 14:
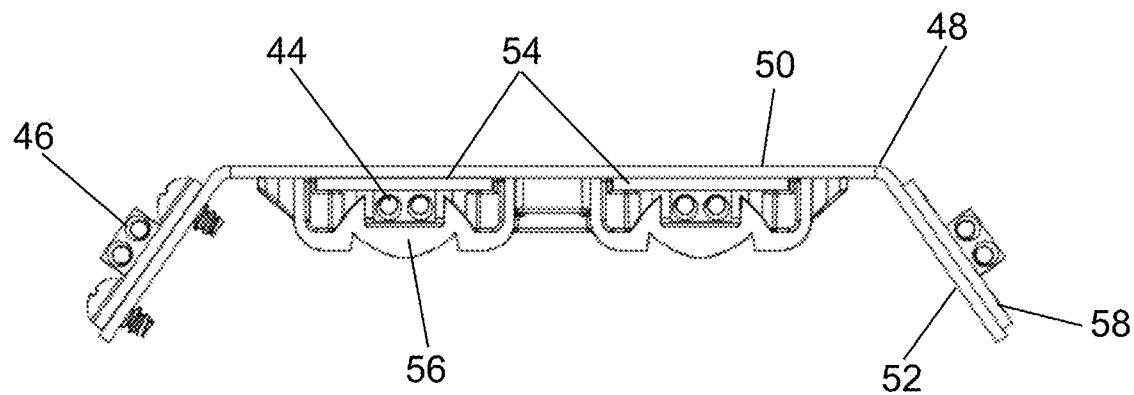
FIG. 14 is a side view the light emitter assembly of FIG. 12.
Figure 15:
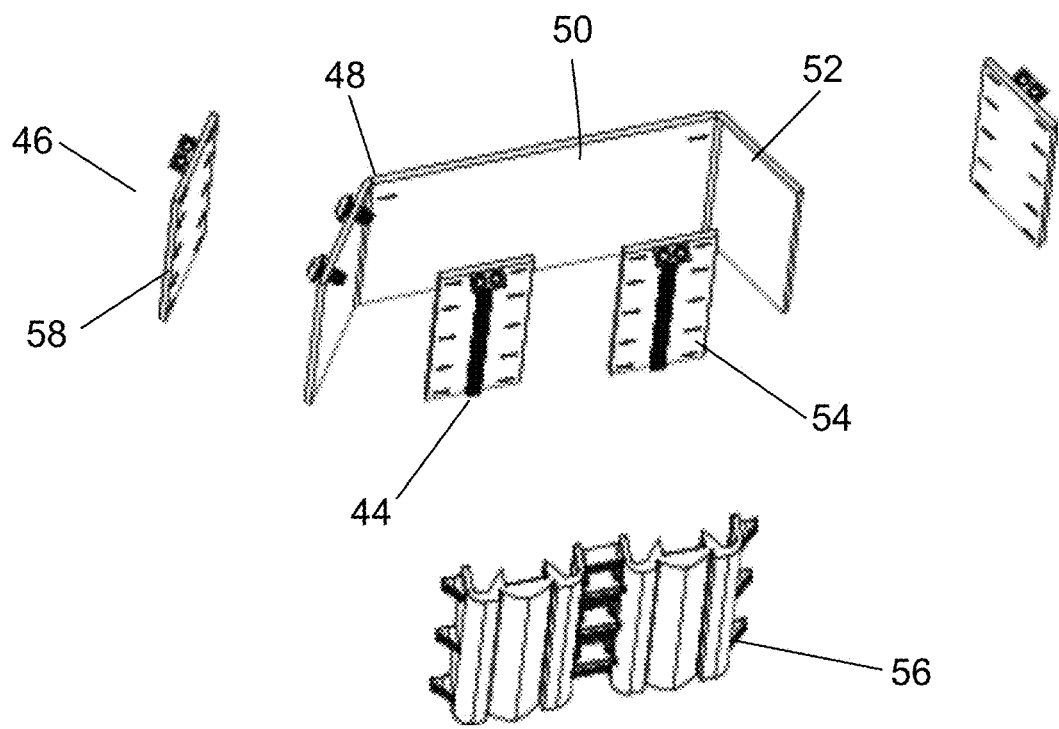
FIG. 15 is an exploded view the light emitter assembly of FIG. 12.
Figure 16:
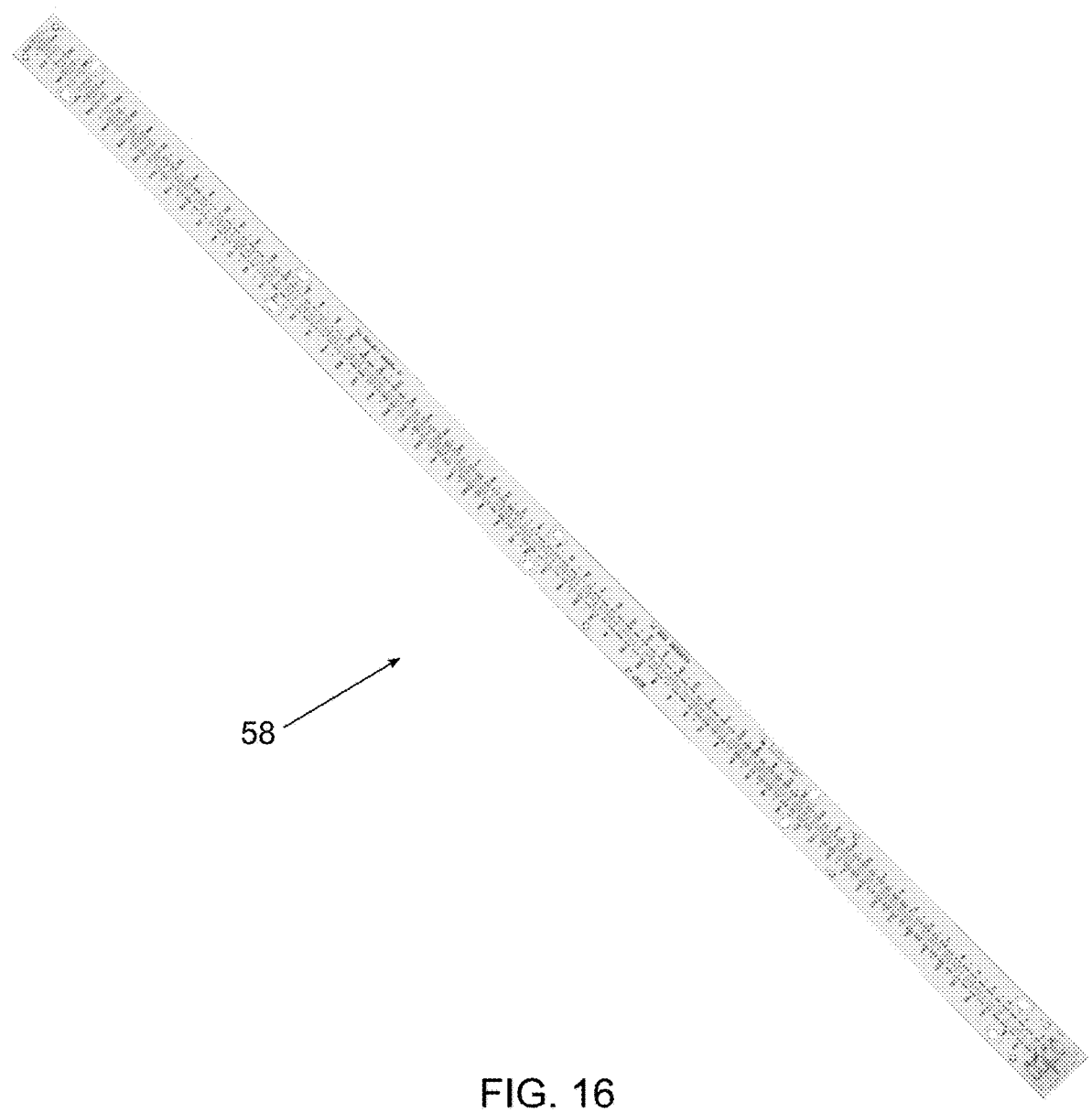
FIG. 16 is a perspective view of an exemplary LED board.
Figure 17:
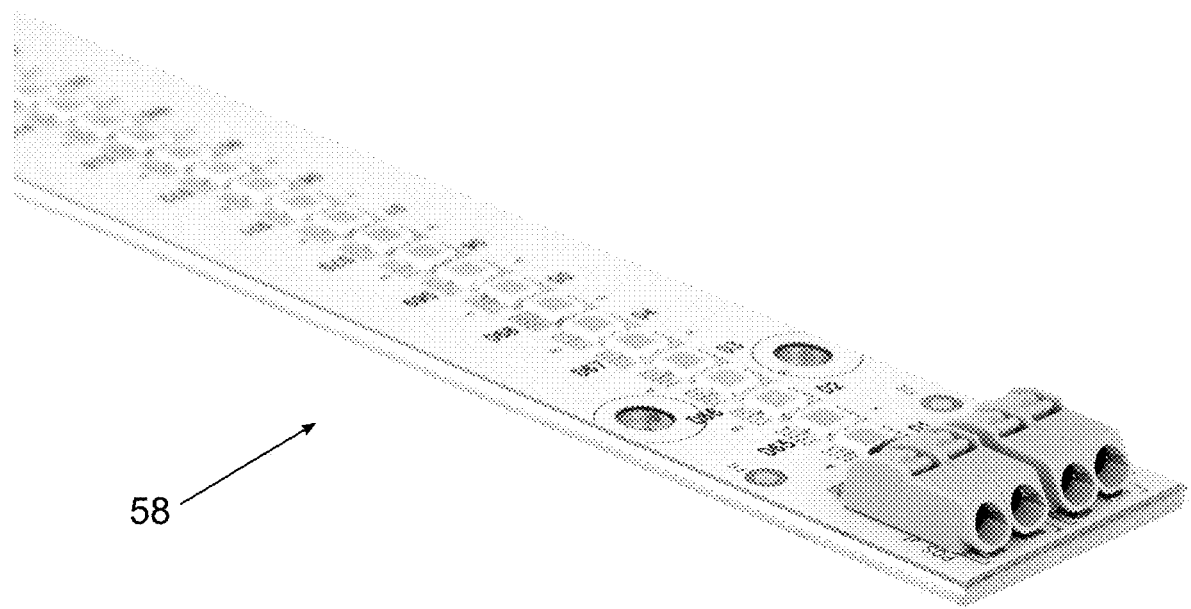
FIG. 17 is a partial view of the LED board of FIG. 16.
Figure 18:
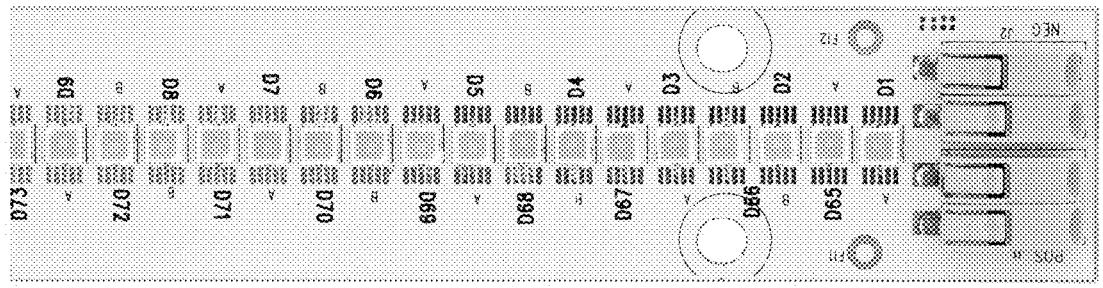
FIG. 18 an upper view of the LED board of FIG. 17.
Figure 19:
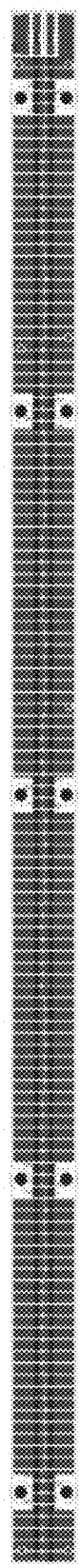
FIGS. 19-21 are upper views of exemplary trace layouts for the LED board.
Figure 20:
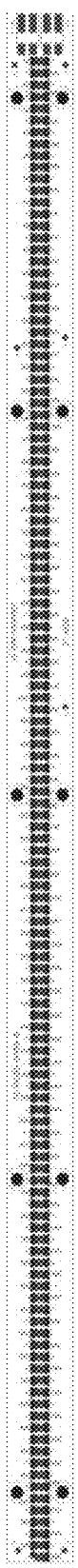
Figure 21:
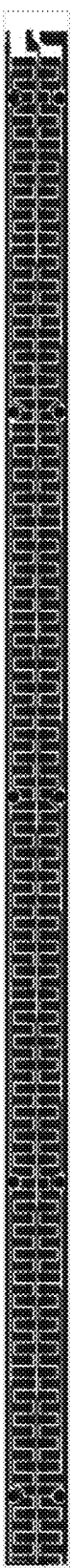

As best shown in FIGS. 14 and 15, the central light emitters 44 include one or more LED boards 54 mounted to the central portion 50 of the support 48. The number of LED boards 54 used depends on the size and the desired light output. In an exemplary embodiment having a 2×4 housing, a set of two, two-foot long LED boards 54 are used on each side, resulting in 4 total LED boards 54 associated with the central light emitters 44. An optic 56 is positioned over the LED boards 54. The LED boards 54 and the optic 56 are connected to the support 48 through one or more fasteners. In an exemplary embodiment, the optic 56 is a total-internal-reflection (TIR) optic.

The side light emitters 46 also include an LED board 58 having one or more LEDs mounted to a printed circuit board. The LED boards 58 are connected to the support 48 through one or more fasteners. The number of LED boards 58 used depends on the size and the desired light output. In an exemplary embodiment having a 2×4 housing, a set of two, two-foot long LED boards 58 are used on each side, resulting in 4 total LED boards 58 associated with the side light emitters 46.

The side light emitters 46 are used to produce light in both the ambient mode and the reading mode. The reading mode has a higher light output than the ambient mode. To accommodate the higher light output, the side light emitters 46 can be controlled to operate in a first mode where a first set of LEDs are activated and in a second mode where the first set and a second set of LEDs are activated. In an exemplary embodiment, the LEDs can be positioned in a single row, with alternating LEDs belonging to the first set or the second set. Each LED board 58 can include a first circuit associated with the first set of LEDs and a second circuit associated with the second set of LEDs. Depending on the mode, one or both of the circuits are activated to power the first set of LEDs or the first and second sets of LEDs.

Figure 22:
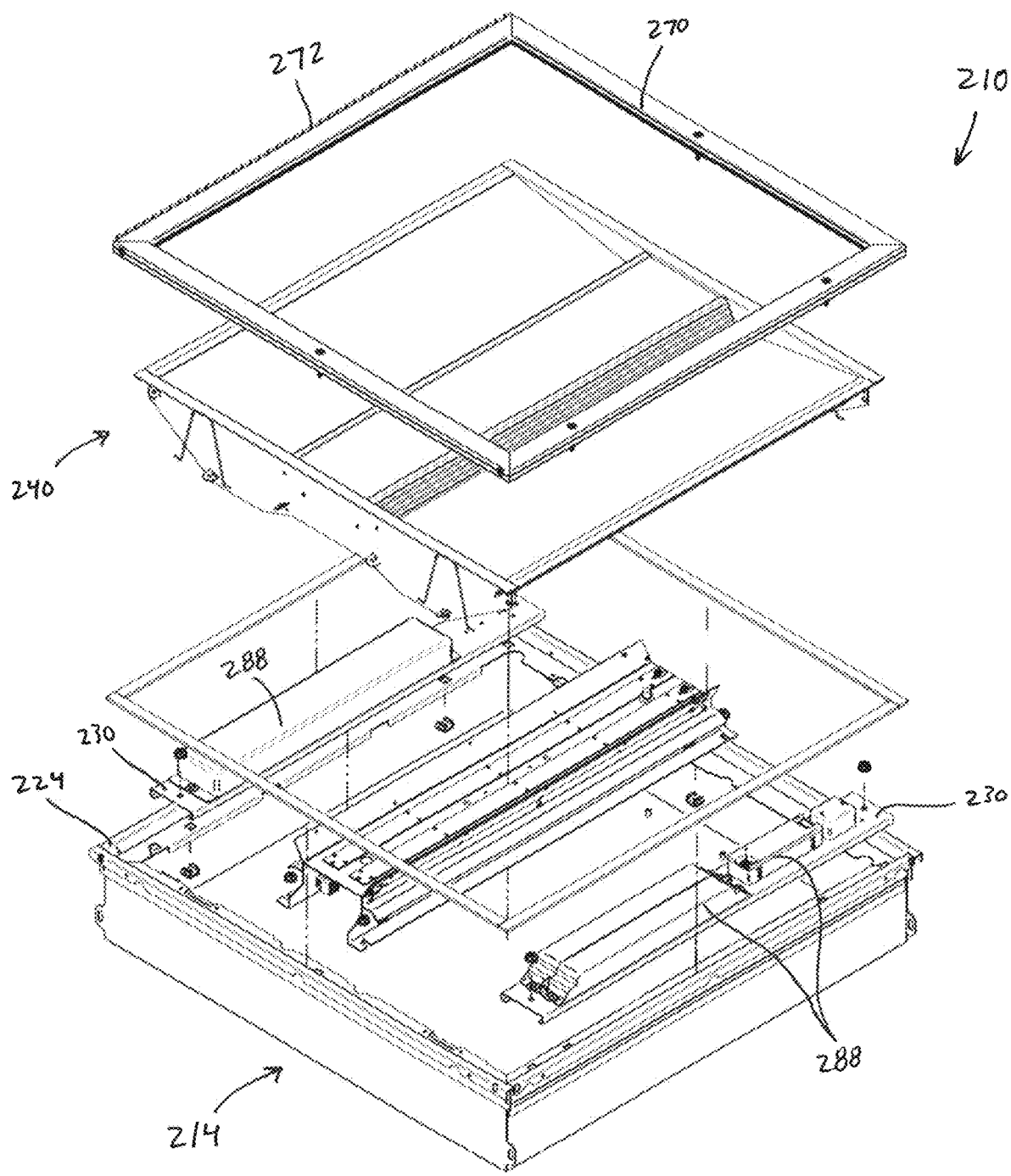
FIG. 22 is an exploded view of a light fixture according to another embodiment.

FIG. 22 illustrates a light fixture 210 according to another embodiment. The light fixture 210 is similar to the light fixture 10 described above, and similar features are identified with similar reference numbers, plus 200. For the sake of brevity, only differences between the light fixture 210 and the light fixture 10 are described in detail.

As shown in FIG. 22, the light fixture 210 includes a door 270 coupled to a flange 224 of a housing 214. The door 270 may include a transparent lens (not shown). The door 270 includes a hinge 272 coupled to the side flange 224 of the housing 214, and the door 270 may pivot relative to the housing 214 about the hinge 272 to provide user access to the housing 214. In other embodiments (FIG. 23), the light fixture 210 may be constructed without a door such that the bottom of the housing 214 is open.

Figure 24:
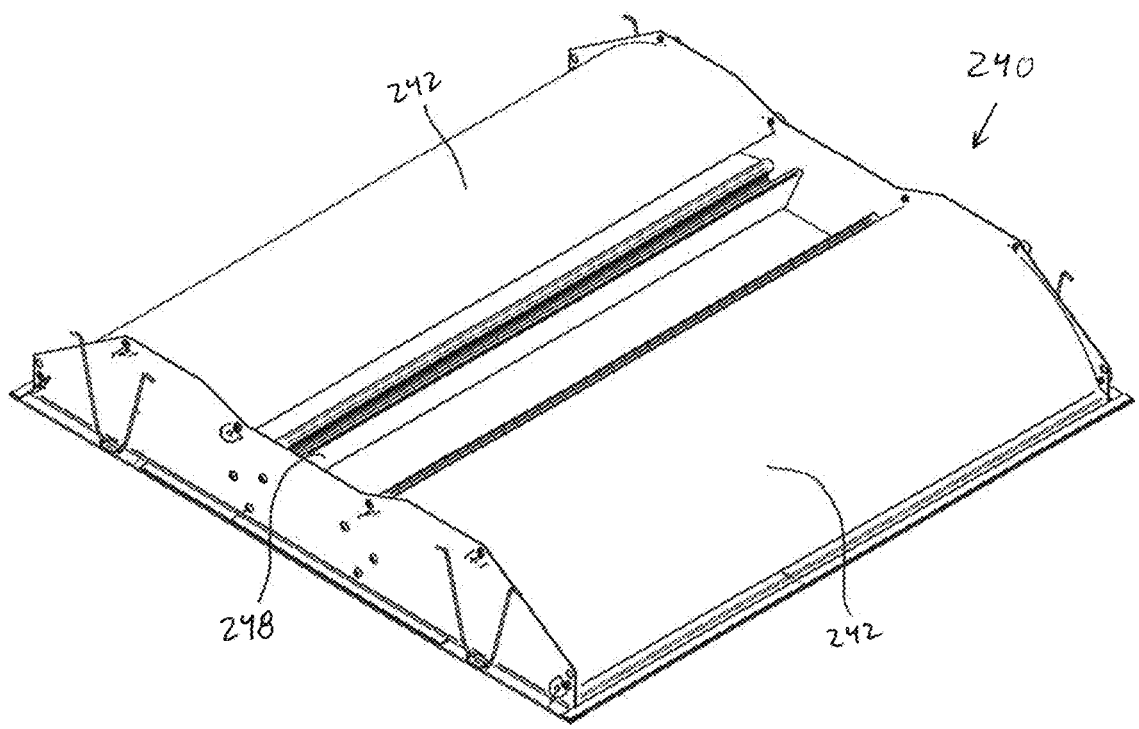
FIG. 24 is a perspective view of a light emitter assembly of the light fixture of FIG. 22.
Figure 25:
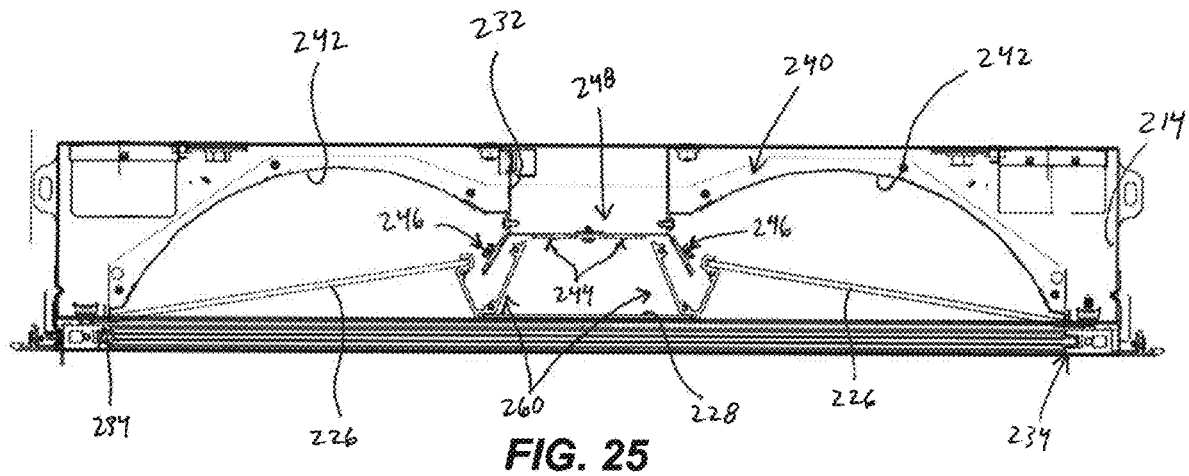
FIG. 25 is a section view of the light fixture of FIG. 22.

In addition, as shown in FIGS. 24 and 25, a light emitter assembly 240 is supported in the housing 214 (FIG. 25). The light emitter assembly 240 includes a central support 248, lens support brackets 260, and reflectors 242 coupled together in a common assembly. As shown in FIG. 25, the central support 248 is coupled to a central bracket 232 of the housing. Central light emitters 244 are coupled to a lower surface of the central support 248, and side light emitters 246 are coupled to angled side portions of the central support 248. A central lens 228 is supported in a central portion of the lens support bracket 260, and the side lenses 226 are supported between the lens support bracket 260 and side brackets 234. In the illustrated embodiment, the light emitters 244, 246 include LED boards similar to the light emitters 44, 46 described above, although the light emitters 244, 246 do not include an optic (e.g., a TIR optic) positioned over the LED boards 54. In other embodiments, the light emitters 244, 246 may include an optic.

Referring again to FIG. 22, the light fixture housing 214 includes trays 230 for supporting a plurality of drivers and/or other control components. In the illustrated embodiment, the light fixture 210 includes three drivers 288. One of the drivers 288 may power some light emitters in a first mode (e.g., ambient/reading mode), another driver 288 may power some light emitters in a second mode (e.g., exam mode), and the other driver 288 may power some light emitters in a third mode (e.g., nightlight mode). In some embodiments, the drivers 288 may be dimmable to allow dimming of the light emitters 244, 246 (FIG. 25).

In addition, in some embodiments the side light emitters 246 may include a first set of LEDs having a first color temperature and a second set of LEDs having a second color temperature. One or more of the driver(s) 288 may adjust the relative current applied to each set of LEDs to adjust the light output mixture from the two sets of LEDs, thereby adjusting the color temperature of the total light output. In some embodiments, the color tuning aspect may be similar to the system described in U.S. Publication No. 2016/0157318, published Jun. 2, 2016 and U.S. Publication No. 2016/0157319, published Jun. 2, 2016, the entire contents of which are hereby incorporated by reference.

Figure 23:
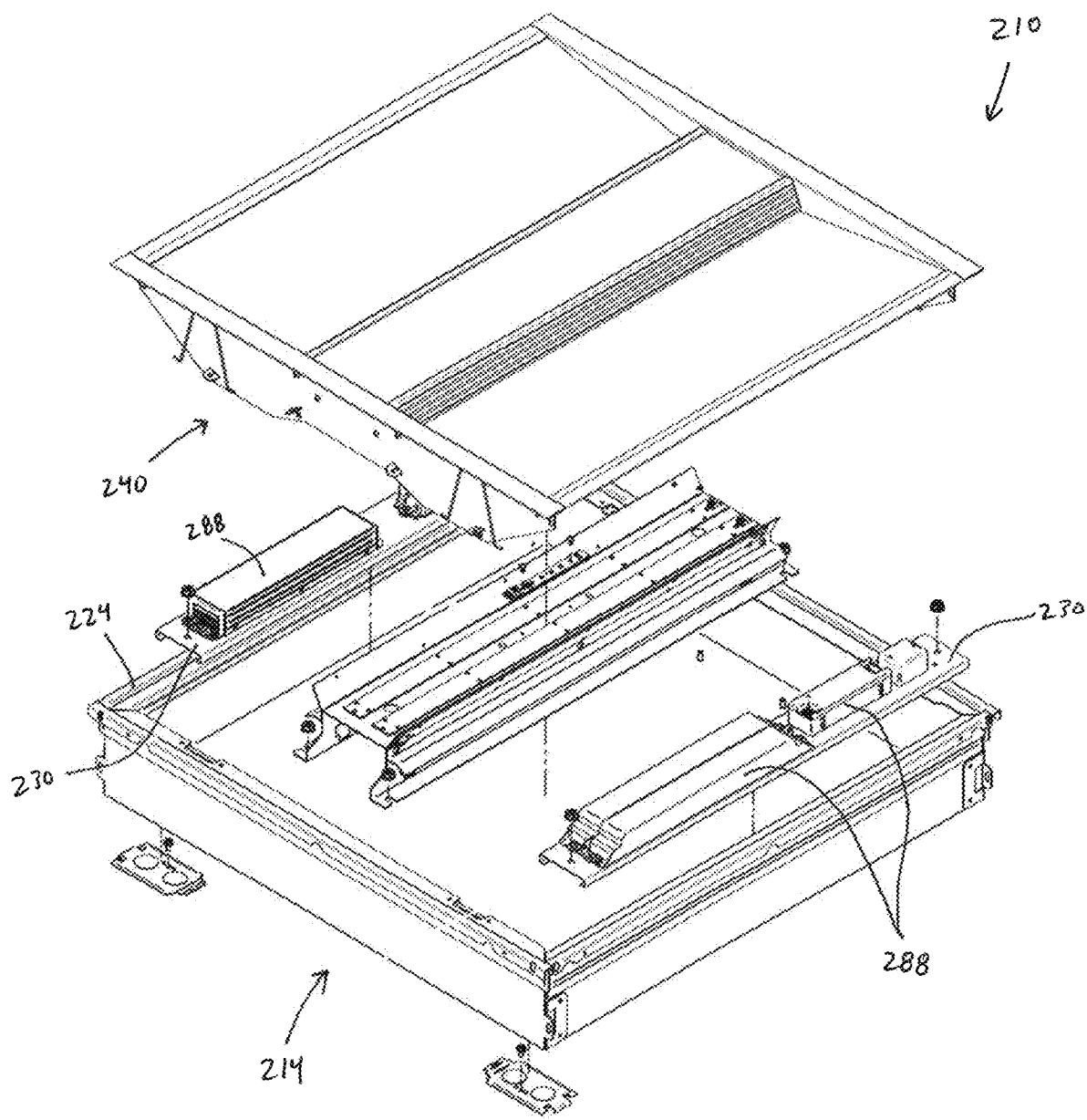
FIG. 23 is an exploded view of a light fixture according to another embodiment.

In some embodiments, the light fixture 210 operates in two primary modes. In a first or ambient/reading mode, only the side light emitters 246 are activated to provide a soft or diffuse light from side portions of the fixture 210. The first mode provides light for an ambient or reading mode. In a second or examination mode, all of the light emitters—the central emitters 244 and the side emitters 246—are activated, and the central emitters 244 provide direct, downward light for patient examination. In addition, as shown in FIG. 23, the light fixture 210 may further include nightlight emitters 290. The light fixture 210 may be operated in a third or nightlight mode, in which only the nightlight emitters 290 are activated.

Figure 26:
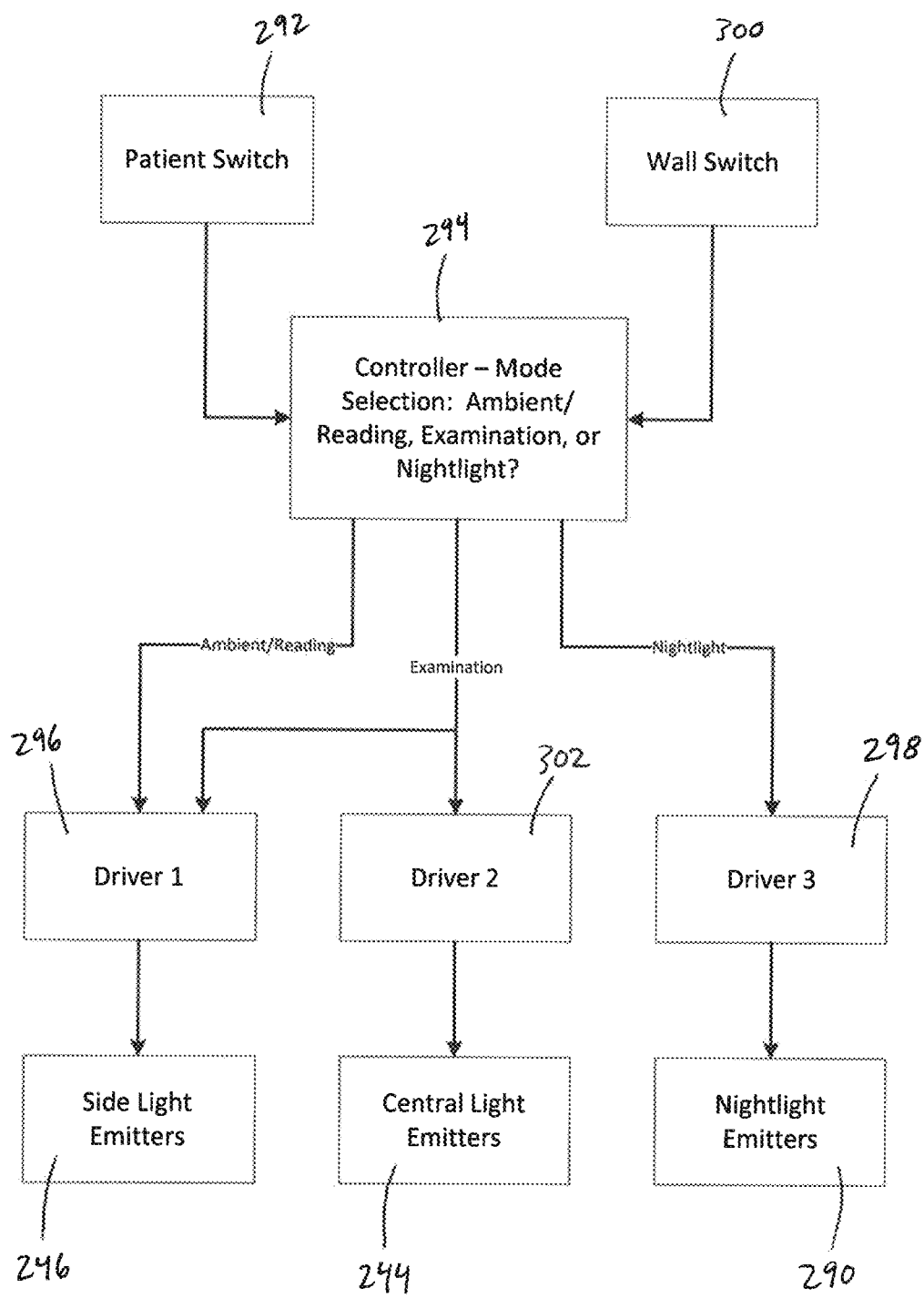
FIG. 26 is a flowchart illustrating a control method for a light fixture.

FIG. 26 illustrates a control system according to one embodiment. A patient switch or "pillow" switch 292 may be configured to select the ambient/reading mode, the nightlight mode, or an off mode. If the ambient mode is selected, a controller 294 passes current to a first circuit including a driver 296 for activating the side light emitters 246. If the nightlight mode is selected, the controller 294 passes current to a third circuit including a driver 298 for activating the nightlight emitters 290. A wall switch 300 may be configured to select the examination mode, in which the controller 294 passes current to both the first circuit and a second circuit including a driver 302 associated with the central light emitters 244. Once the examination mode is cycled off, the controller 294 may return the first circuit to its previous state (i.e., off or ambient/reading mode).

The foregoing detailed description of certain exemplary embodiments has been provided for the purpose of explaining the general principles and practical application, thereby enabling those skilled in the art to understand the disclosure for various embodiments and with various modifications as are suited to the particular use contemplated. This description is not necessarily intended to be exhaustive or to limit the disclosure to the exemplary embodiments disclosed. Modifications may be made to adapt a particular situation or material to the teachings of the disclosure without departing from the scope thereof. Any of the embodiments and/or elements disclosed herein may be combined with one another to form various additional embodiments not specifically disclosed. Accordingly, additional embodiments are possible and are intended to be encompassed within this specification and the scope of the appended claims. The specification describes specific examples to accomplish a more general goal that may be accomplished in another way.

As used in this application, the terms "front," "rear," "upper," "lower," "upwardly," "downwardly," and other orientational descriptors are intended to facilitate the description of the exemplary embodiments of the present disclosure, and are not intended to limit the structure of the exemplary embodiments of the present disclosure to any particular position or orientation. Terms of degree, such as "substantially" or "approximately" are understood by those of ordinary skill to refer to reasonable ranges outside of the given value, for example, general tolerances associated with manufacturing, assembly, and use of the described embodiments.

We claim:

1. A light fixture comprising:
a housing having an upper wall configured to be positioned proximate a ceiling and a plurality of side walls at least partially defining an opening, the housing extending along a longitudinal axis;
a frame coupled to at least one of the plurality of side walls of the housing proximate to the opening and configured to securely mount and support the housing with respect to the ceiling;
a lens assembly including a central lens and a pair of side lenses, the central lens extending along the longitudinal axis of the housing, each side lens extending parallel to the central lens and positioned on a lateral side of the central lens;
at least one central light emitter for emitting light directly through the central lens generally away from the ceiling;
a pair of side light emitters, light emitted by each side light emitter passing through an associated one of the side lenses and generally away from the ceiling; and
at least one control component operatively connected to the at least one central light emitter and the side light emitters,
wherein the at least one control component is configured to operate in a first mode in which the at least one central light emitter is deactivated and the side light emitters are activated, and a second mode in which the at least one central light emitter and the side light emitters are activated.

2. The light fixture of claim 1, wherein the one or more control components are supported on a tray in the housing.

3. The light fixture of claim 2, wherein the tray is removable from the housing.

4. The light fixture of claim 1, wherein each central light emitter is directed toward the opening and each side light emitter is directed away from the opening at an oblique angle.

5. The light fixture of claim 4, wherein a pair of reflectors are positioned in the housing to reflect light from an associated one of the side light emitters toward the side lens.

6. The light fixture of claim 1, further comprising an outer lens supported on the housing and positioned in the opening.

7. The light fixture of claim 1, further comprising at least one nightlight emitter, wherein the at least one control component is further configured to operate in a third mode in which the at least one nightlight emitter in activated and the at least one central light emitter and the side light emitters are deactivated.

8. The light fixture of claim 1, wherein the frame extends across the upper wall.

9. A light fixture comprising:
a housing having an upper wall configured to be positioned proximate a ceiling and a plurality of side walls at least partially defining an opening;
a frame coupled to at least one of the plurality of side walls of the housing proximate to the opening and configured to securely mount and support the housing with respect to the ceiling;
a light emitter assembly positioned in the opening and secured to the housing, the light emitter assembly including,
a central portion including a plurality of central light emitters aligned along an axis and configured to emit light generally away from the ceiling,
a first side portion positioned on one side of the central portion and including a plurality of first side light emitters aligned in a direction parallel to the axis and configured to emit light generally away from the ceiling,
a second side portion positioned on another side of the central portion and including a plurality of second side light emitters aligned in a direction parallel to the axis and configured to emit light generally away from the ceiling, and
a lens assembly including a central lens, a first side lens, and a second side lens, the central lens positioned adjacent the plurality of central light emitters, the first side lens positioned adjacent the plurality of first side light emitters, the second side lens positioned adjacent the plurality of second side light emitters; and
at least one control component operatively connected to the central light emitters, the first side light emitters, and the second side light emitters, the at least one control component configured to operate in a first mode in which the first side light emitters and the second side light emitters are activated and configured to operate in a second mode in which the first side light emitters, the second side light emitters, and the central light emitters are activated.

10. The light fixture of claim 9, wherein each central light emitter is directed toward the opening and each side light emitter is directed away from the opening at an oblique angle.

11. The light fixture of claim 10, wherein the light emitter assembly further includes a pair of reflectors, each of the reflectors reflecting light from an associated one of the first side light emitters and the second side light emitters toward an associated one of the first side lens and the second side lens.

12. The light fixture of claim 9, further comprising an outer lens supported on the housing and positioned in the opening.

13. The light fixture of claim 9, further comprising at least one nightlight emitter, wherein the at least one control component is further configured to operate in a third mode in which the at least one nightlight emitter in activated and the central light emitters, the first side light emitters, and the second side light emitters are deactivated.

14. The light fixture of claim 9, wherein the plurality of first side light emitters includes a first set of light emitters and a second set of light emitters.

15. The light fixture of claim 14, wherein a first circuit controls the first set of light emitters and a second circuit controls the second set of light emitters.

16. A method for controlling operation of a light fixture, the method comprising:
   providing a housing having an upper wall configured to be positioned proximate a ceiling and a plurality of side walls at least partially defining an opening;
   providing a frame coupled to at least one of the plurality of side walls of the housing proximate to the opening and configured to securely mount and support the housing with respect to the ceiling;
   determining which mode of a plurality of modes is selected;
   while a first mode is selected, activating a plurality of first side light emitters, activating a plurality of second side light emitters, and deactivating a plurality of central light emitters positioned between the first side light emitters and the second side light emitters; and
   while a second mode is selected, activating the plurality of first side light emitters, the plurality of second side light emitters, and the plurality of central light emitters.

17. The method of claim 16, further comprising transmitting a signal from at least one of patient switch and a wall switch to a controller, wherein the patient switch is configured to transmit a signal indicative of the first mode, wherein the wall switch is configured to transmit at least a signal indicative of the second mode.

18. The method of claim 17, wherein the wall switch is configured to selectively transmit a first signal indicative of the first mode and a second signal indicative of the second mode.

19. The method of claim 16, further comprising, while a third mode is selected, activating a plurality of nightlight emitters and deactivating the plurality of first side light emitters, the plurality of second side light emitters, and the plurality of central light emitters.

20. The method of claim 16, wherein, in the first mode, a portion of the plurality of first side light emitters is activated and a portion of the plurality of second side light emitters is activated, wherein, in the second mode, all of the plurality of first side light emitters is activated and all of the plurality of second side light emitters in activated.

* * * * *